(12) United States Patent
Wright et al.

(10) Patent No.: US 8,058,430 B2
(45) Date of Patent: Nov. 15, 2011

(54) BIOLOGICALLY ACTIVE APHROCALLISTIN COMPOUNDS

(75) Inventors: Amy E. Wright, Fort Pierce, FL (US); Susan H. Sennett, Sebastian, FL (US); Shirley A. Pomponi, Ft. Pierce, FL (US); Peter J. McCarthy, Vero Beach, FL (US); Esther A. Guzman, Fort Pierce, FL (US)

(73) Assignee: Florida Atlantic University Broad of Trustees, Boca Raton, FL (US)

( * ) Notice: Subject to any disclaimer, the term of this patent is extended or adjusted under 35 U.S.C. 154(b) by 551 days.

(21) Appl. No.: 12/165,304

(22) Filed: Jun. 30, 2008

(65) Prior Publication Data

US 2009/0005400 A1    Jan. 1, 2009

Related U.S. Application Data

(60) Provisional application No. 60/947,157, filed on Jun. 29, 2007.

(51) Int. Cl.
*C07D 473/34* (2006.01)
*A61K 31/52* (2006.01)
*A61P 35/00* (2006.01)

(52) U.S. Cl. ..................................................... 544/277
(58) Field of Classification Search .................. 544/277; 514/263.4
See application file for complete search history.

(56) References Cited

U.S. PATENT DOCUMENTS

| | | | |
|---|---|---|---|
| 5,252,569 A * | 10/1993 | Hajos et al. | 514/217.06 |
| 5,543,423 A | 8/1996 | Zelle et al. | |
| 5,723,459 A | 3/1998 | Armistead et al. | |
| 7,094,803 B2 | 8/2006 | Killday et al. | |
| 7,179,828 B2 | 2/2007 | Wright et al. | |
| 2005/0009901 A1 | 1/2005 | Wright et al. | |
| 2006/0264499 A1 | 11/2006 | Wright et al. | |

OTHER PUBLICATIONS

Barrand, M.A. et al., "Multidrug Resistance-Associated Protein: A Protein Distinct from P-glycoprotein Involved in Cytotoxic Drug Expulsion," *General Pharmacology*, 1997, vol. 28, No. 5, pp. 639-645.

Bellamy, W.T., "P-Glycoproteins and Multidrug Resistance," *Annu. Rev. Pharmacol. Toxicol.*, 1996, vol. 36, pp. 161-183.
Broxterman, H.J. et al., "Multidrug Resistance Proteins and Other Drug Transport-Related Resistance to Natural Product Agents," *Current Opinion in Oncology*, 1995, vol. 7, pp. 532-540, Abstract only.
Komarov, P.G. et al. "Activation of the LRP (lung resistance-related protein) gene by short-term exposure of human leukemia cells to phorbol ester and cytarabine," *Oncology Research*, 1998, vol. 10, pp. 185-192, Abstract only.
Krishan, A. et al., "Drug Retention, Efflux, and Resistance in Tumor Cells," *Cytometry*, 1997, vol. 29, pp. 279-285.
Miller, D. W. et al., "The expression of multidrug resistance-associated protein (MRP) in pancreatic adenocarcinoma cell lines," *Cancer Letters*, 1996, vol. 107, pages 301-306.

* cited by examiner

*Primary Examiner* — Mark Berch
(74) *Attorney, Agent, or Firm* — Saliwanchik, Lloyd & Eisenschenk

(57) ABSTRACT

The subject invention provides novel compositions of biologically active compounds which can advantageously be used in blocking cellular proliferation and/or treatment of cancer. Exemplified are:

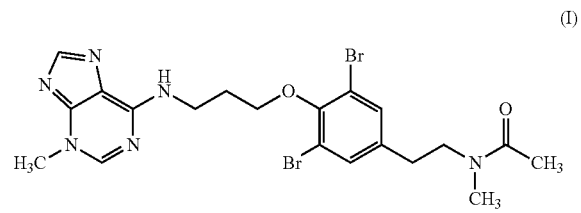

Aphrocallistin A and

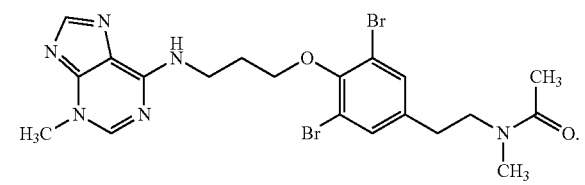

Aphrocallistin B

1 Claim, 1 Drawing Sheet

BIOLOGICALLY ACTIVE APHROCALLISTIN COMPOUNDS

CROSS-REFERENCE TO A RELATED APPLICATION

The subject application claims the benefit of U.S. Provisional Application Serial No. 60/947,157, filed Jun. 29, 2007, which is hereby incorporated by reference in its entirety.

GOVERNMENT SUPPORT

This invention was made with government support under a grant awarded from the National Institute of Health/National Cancer Institute under grant number 1RO1-CA-093455. The government has certain rights in the invention.

FIELD OF THE INVENTION

This invention relates to organic compounds and compositions which have useful therapeutic properties. More particularly, the invention concerns novel compounds having anti-proliferative and antitumor activities, pharmaceutical compositions comprising such compounds, and methods of their use for therapeutic purposes.

BACKGROUND OF THE INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antitumor chemical compositions are needed. Anti-proliferative agents can also be useful in treating autoimmune diseases and inflammatory disease.

In searching for new biologically active compounds, it has been found that some natural products and organisms are potential sources for chemical molecules having useful biological activity of great diversity. For example, the diterpene commonly known as paclitaxel, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219-1222; Schiff, P. B., J. Fant, S. B. Horwitz [1979] *Nature* (London) 22:665-667). Paclitaxel is also known to have antitumor activity and has undergone a number of clinical trials which have shown it to be effective in the treatment of a wide range of cancers (Rowinski, E. K. R. C. Donehower [1995] *N. Engl. J. Med.* 332:1004-1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978-1983, Vol. I-V; Uemura, D., K. Takahashi, T. Yamamoto, C. Katayama, J. Tanaka, Y. Okumura, Y. Hirata (1985) *J. Am. Chem. Soc.* 107:4796-4798; Minale, L. et al. (1976) *Fortschr. Chem. org. Naturst.* 33:1-72 Faulkner, D. J., *Nat. Prod. Reports* 1984, 1, 251-551; ibid. 1987, 4, 539; ibid 1990, 7, 269; ibid 1993, 10, 497; ibid 1994, 11, 355; ibid 1995, 12, 22; ibid 1998, 15:113-58; ibid 2000 17:1-6; ibid 2000 17: 7-55; ibid 2001, 18: 1-49; 2002, 19: 1-48; Gunasekera, S. P., M. Gunasekera, R. E. Longley and G. K. Schulte (1990) *J. Org. Chem.,* 55:4912-4915; Horton, P. A., F. E. Koehn, R. E. Longley, and O. J. McConnell, (1994) *J. Am. Chem. Soc.* 116: 6015-6016.

The success of chemotherapy for the treatment of various cancers can be substantially negated though cellular mechanisms which have evolved to enable neoplastic cells to subvert the cytotoxic effects of the drug. Some cells have developed mechanism that confer resistance to a number of structurally unrelated drugs. This multi-drug resistance (or MDR) phenomenon may arise through a number of different mechanisms. One of these involves the ability of a cell to reduce intracellular concentrations of a given drug through efflux from cytoplasm through and out the cell membrane by a series of unique ATP-dependent transporter proteins called-P-glycoproteins (Pgp) (Casazza, A. M. and C. R. Fairchild [1996] "Paclitaxel (Taxol®): mechanisms of resistance" *Cancer Treat Res.* 87:149-171). The surface membrane, 170 kDa Pgp, is encoded by the mdr-1 gene and appears to require substrate binding before transport begins. A wide range of compounds. including a number of structurally unrelated chemotherapeutic agents (adriamycin, vinblastine, colchicine, etoposide and Taxol), are capable of being transported by Pgp and render the cell resistant to the cytotoxic effects of these compounds.

While many normal cell types possess Pgp, in general, tumor cell lines, which possess high levels of mRNA specific for Pgp, also exhibit overexpression of membrane Pgp and demonstrate resistance to various drugs. This intrinsic resistance can be increased multifold by incubation of cells with stepwise increasing doses of a particular drug over a period of several months. This can be further facilitated by the addition of the MDR reversal agent, verapamil (Casazza, A. M. and C. R. Fairchild [1996] supra) in combination with the particular drug. Drug resistant cell lines produced in this fashion exhibit resistance to drug cytotoxicity from 20 to 500 fold, compared to parental cell lines.

An additional target for cancer drug discovery is a high molecular weight membrane protein associated with multidrug resistance properties of certain tumor cells known as the multidrug resistance-associated protein (MRP). MRP is a 190 kD membrane-bound glycoprotein (Bellamy, W. T. [1996], Annu. Rev. Pharmacol. Toxicol., 36: 161-183.) which belongs to the same family of proteins as the p-glycoprotein pump P-gp (Broxterman, H. J., Giaccone, G., and Lankelma, J. [1995], Current Opinion in Oncology, 7:532-540.) but shares less than 15% homology of amino acids with P-gp (Komorov, P. G., Shtil, A. A., Holian, O., Tee, L., Buckingham, L., Mechetner, E. B., Roninson, I. B., and Coon, J. S. [1998], Oncology Research, 10: 185-192.). MRP has been found to occur naturally in a number of normal tissues, including liver, adrenal, testis, and peripheral blood mononuclear cells (Krishan, A., Fitz, C. M., and Andritsch, I. [1997], Cytometry, 29: 279-285). MRP has also been identified in tissues of the lung, kidney, colon, thyroid, urinary bladder, stomach, spleen (Sugawara, I. [1998] The Cancer Journal, 8(2) and skeletal muscle (Kruh, G. D., Gaughan, K. T., Godwin, A., and Chan, A. [1995], Journal of the National Cancer Institute, 87(16): 1256-1258). High levels of MRP have been implicated in multidrug resistance (MDR) in cancers of the lung and pancreas (Miller, D. W., Fontain, M., Kolar, C., and Lawson, T. [1996]. Cancer Letters, 107: 301-306), and in neuroblastomas, leukemias and cancer of the thyroid (Kruh, G. D., Gaughan, K. T., Godwin, A., and Chan, A. [1995], Journal of the National Cancer Institute, 87(16): 1256-1258), as well as bladder, ovarian and breast cancers (Barrand, M., Bagrij, T., and Neo, S. [1997], General Pharmacology, 28(5): 639-645).

MRP-mediated MDR involves some of the same classes of compounds as those which are mediated by P-gp, including vinca alkaloids, epipodophyllotoxins, anthracyclins and actinomycin D (Barrand, M., Bagrij, T., and Neo, S. [1997], General Pharmacology, 28(5): 639-645). However, the substrate specificity has been demonstrated to differ from that of P-gp (Komorov, P. G., Shtil, A. A., Holian, O., Tee, L., Buckingham, L., Mechetner, E. B., Roninson, I. B., and Coon, J. S. [1998], Oncology Research, 10: 185-192). Drugs which would inhibit or which are not substrates for the MDR pump would, therefore, be useful as chemotherapeutic agents.

BRIEF SUMMARY OF THE INVENTION

The subject invention is provides novel compositions of biologically active compounds that have utility in inhibiting cellular proliferation. In a specific embodiment, the compounds and compositions of the subject invention can be used in the treatment of cancer, including multi-drug resistant cancers.

The subject invention provides compounds of the following structure:

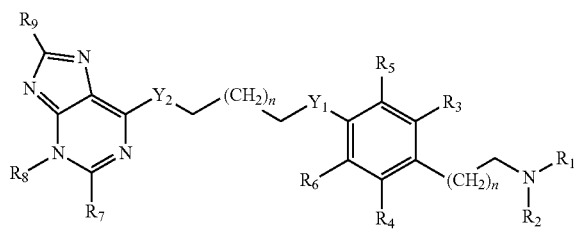

wherein $R_{1-9}$ are the same or different and are selected from —H, —OH, halogen, —R, —OR, —COR, —OA, and NZZ (wherein the Zs can be the same or different);

$Y_1$ is NZ, O, or S;

$Y_2$ is NZ, O, or S;

Z is independently selected from —H, —R, —OH, and —COR;

R is C1-C8 alkyl or C1-C8 alkoxyl, mesyl, or tosyl;

A is —R-phenyl; and n is 1-6.

In a preferred embodiment:

$R_1$ is COR;

$R_2$ is $CH_3$;

n is 1;

$R_3=R_4=H$;

$R_5=R_6=Br$;

$R_7=R_9=H$; and $R_8=CH_3$.

One aspect of the current invention concerns the novel compounds aphrocallistin A (I) and B (II). Advantageously, these compounds can inhibit unwanted cellular proliferation, including the proliferation of tumor cells.

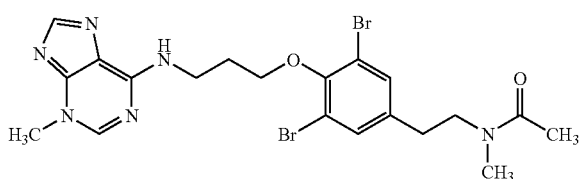

Aphrocallistin A

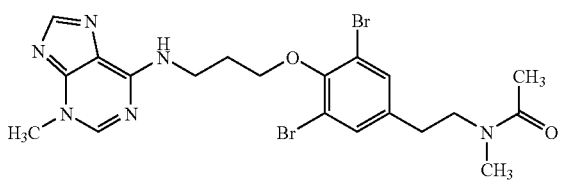

Aphrocallistin B

In a specific embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, liver, pancreatic, uterine, or lung tumors, as well as human leukemia or melanoma cells. The mechanisms for achieving anti-cancer activity exhibited by the subject compounds would lead a person of ordinary skill in the art to recognize the applicability of the subject compounds, compositions, and methods to additional types of cancer as described herein.

In specific embodiments, the subject invention provides new compounds, as exemplified by Aphrocallistin A (I) and Aphrocallistin B. Aphrocallistins A and B have not been isolated previously from a natural source nor have they been previously synthesized. One embodiment of the subject invention provides an approximately 3:2 mixture of these compounds with anti-cancer activity.

In accordance with the subject invention, methods for inhibiting cancer cells in a host include contacting tumor cells with an effective amount of the new pharmaceutical compositions of the invention. The cancer cells inhibited by the invention are those which are susceptible to the subject compounds described herein or compositions comprising those compounds.

Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE OF THE INVENTION

Figure 1:
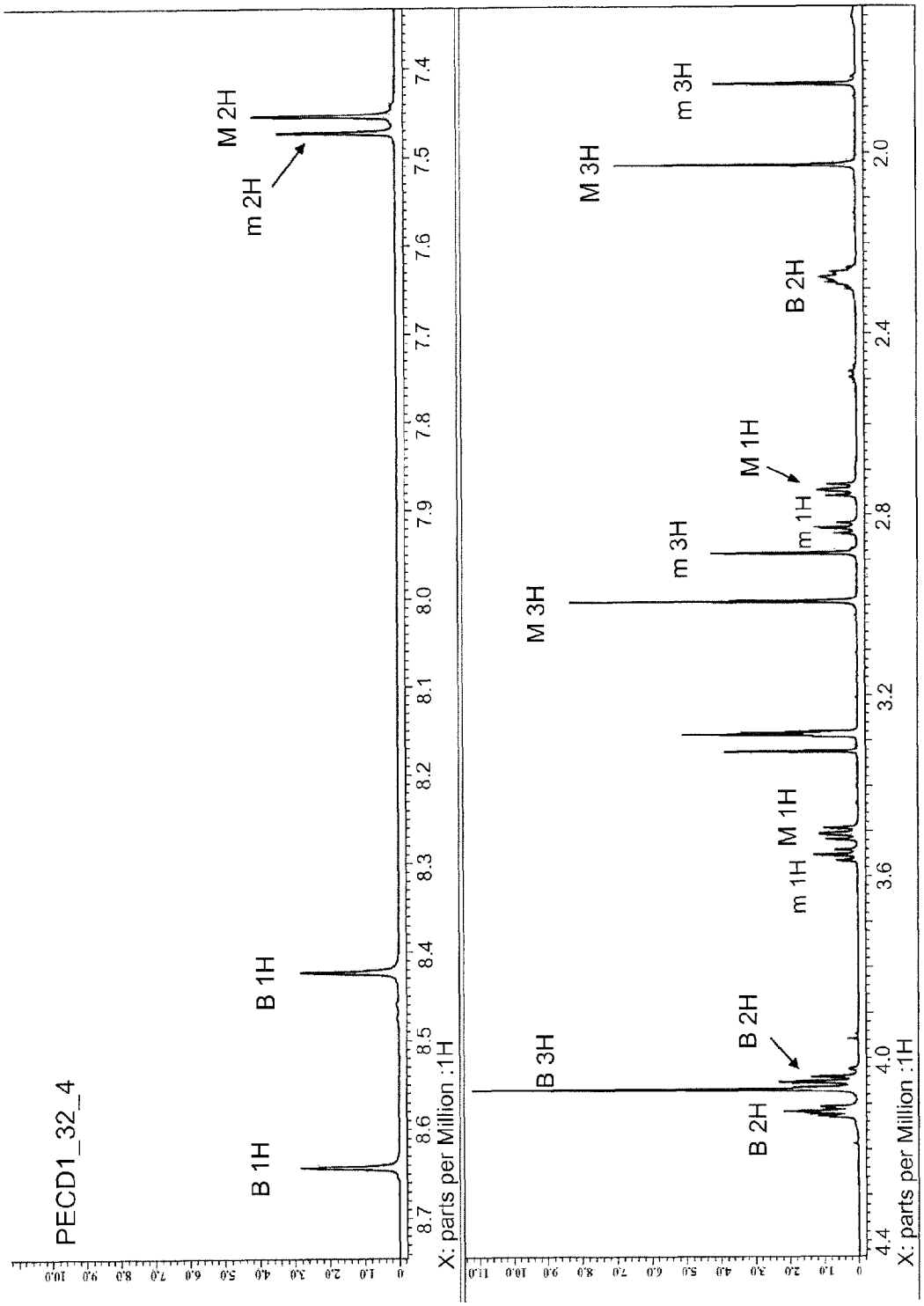
FIG. 1 shows a NMR Spectrum of Aphrocallistins A and B as a 3:2 mixture A:B (600 MHZ, 4-methanol).

The subject invention provides novel compositions of biologically active compounds that are useful for inhibiting pathological cellular proliferation. In a preferred embodiment, these compounds can be used for treating cancer.

More specifically, the novel compounds, compositions and methods of use can advantageously be used to inhibit the growth of tumor and other cancer cells in a mammalian host. More particularly, the subject compounds can be used for inhibiting in a human the growth of tumor cells, including cells of breast, prostate, colon, CNS, ovarian, renal, liver, pancreatic, uterine, or lung tumors, as well as human leukemia or melanoma cells. The compounds also have utility in the treatment of multi-drug resistant cancer cells.

The subject invention provides compounds of the following structure:

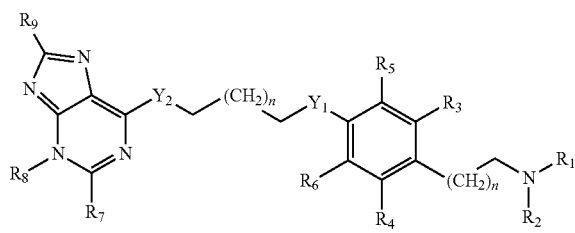

wherein $R_{1-9}$ are the same or different and are selected from —H, —OH, halogen, —R, —OR, —COR, —OA, and NZZ (wherein the Zs can be the same or different);

$Y_1$ is NZ, O, or S;

$Y_2$ is NZ, O, or S:

Z is independently selected from —H, —R, —OH, and —COR;

R is C1-C8 alkyl or C1-C8 alkoxyl, mesyl, or tosyl;

A is —R-phenyl; and n is 1-6

In a preferred embodiment:

$R_1$ is COR;

$R_2$ is CH3;

n is 1;

$R_3$=$R_4$=H;

$R_5$=$R_6$=Br;

$R_7$=$R_9$=H; and $R_8$=$CH_3$

In a preferred embodiment, the subject invention provides compounds having the following formula:

(I)

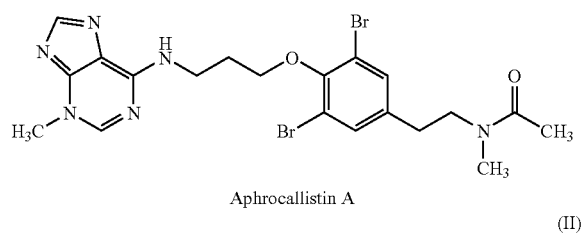

Aphrocallistin A (II)

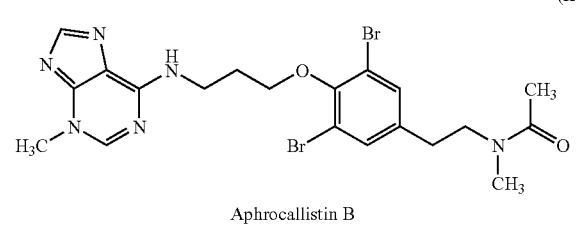

Aphrocallistin B

In accordance with the subject invention, methods for inhibiting cancer in a host include contacting cancer cells with an effective amount of the new pharmaceutical compositions of the invention. The tumor cells inhibited by the invention are those which are susceptible to the subject compounds described herein or compositions comprising those compounds.

The subject invention further provides methods of use of the new compounds and compositions of the invention, e.g., methods of inhibiting tumors and other cancer cells in an animal, preferably a mammal. Most preferably, the invention comprises a method for the antitumor treatment of a human in need of such treatment, i.e., a human hosting cancer cells, including breast, colon, liver, pancreatic, uterine, or lung tumor cells, or leukemia cells including multi-drug resistant cancer cells.

In preferred embodiments of the invention, the compounds are substantially pure, i.e., contain at least 95% of the compound as determined by established analytical methods.

In further preferred methods of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

As used in this application, the terms "analogs," refers to compounds which are substantially the same as another compound but which may have been modified by, for example, adding or removing side groups.

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

Example 1

Isolation and Structure Elucidation of Aphrocallistins A (I) and B (II)

A. Collection and Taxonomy of the Source Organism.

A sample of the sponge *Aphrocallistes beatrix* Gray, 1858 (Phylum: Porifera, Class Hexactinellida, Sub Class Hexasterophora Order Hexactinosida, Family Aphrocallistidae) was collected by maimed submersible at a depth of 725.4 m approximately 40 nautical miles east of Fort Pierce on the Fort Pierce Pinnacles, Lophelia Pinnacle #TS-4 (latitude 27 39.4305'N, longitude 79 34.9679'W). The sponge is vasiform with the appearance of folded plates and fingers. It is crispy in texture and friable. It was collected growing in association with yellow sponge zooanthids. A reference sample preserved in ethanol has been deposited in the Harbor Branch Oceanographic Museum (catalog number 02:00022, DBMR number 20-V-04-1-005) and is available for taxonomic evaluation by those skilled in the art.

B. Isolation and Structure Elucidation of Aphrocallistins A (I) and B (II).

Isolation of Aphrocallistins A and B.

The frozen sponge (106 g) was diced and extracted exhaustively with ethanol (Pharmco 100%). The combined ethanol extracts were concentrated to dryness and the residue partitioned between ethyl acetate and water. The ethyl acetate partition was concentrated to dryness to yield 0.493 g of an oil. The residue from the ethyl acetate partition was chromatographed by vacuum flash chromatography on a custom prepared RP-18 stationary phase using a step gradient of $H_2O$—$CH_3CN$—IPA as eluent. Column size was 150 mL. The eluent series is as follows: fraction 1, 100 mL of $H_2O$—$CH_3CN$ (80:20 v/v); fraction 2, 100 mL of $H_2O$—$CH_3CN$ (60:40 v/v); fraction 3, 100 mL of $H_2O$—$CH_3CN$ (40:60 v/v); fraction 4, 100 mL of $H_2O$—$CH_3CN$ (20:80 v/v); fraction 5, 100 mL of $CH_3CN$; Fraction 6 100 mL of $H_2O$—$CH_3CN$: TFA (20:80:0.1 v/v); Fraction 7: 100% $CH_3CN$; Fraction 8: 100% isopropanol. Fractions 6 and 7 (84.4 mg) were further purified by medium pressure liquid chromatography on a C-18 reversed-phase stationary phase using the COMBI-FLASH® COMPANION® with the following gradient program [Solvent A: $H_2O/CH_3CN$/TFA 95:5:0.1 in water v/v; Solvent B: $CH_3CN$/TFA 100:0.1; t=0 minutes, A:B (100:0) hold for 1 minute; t=1 minutes A:B (100:0); t=11 minutes A:B (70:30); t=17 minutes, A:B (0:100); flow=15 mL/min; Detected by uv absorption observed at 230 nm] to yield 40 mg of an inseparable mixture of Aphrocallistin A:B. in the proportions 3 parts Aphrocallistin A to 2 parts Aphrocallistin B. Aphrocallistin A (I) Aphrocallistin B (mixture in proportion of 3:2, respectively): brown oil; MS: m/z observed 539.042786, calculated 539.040571 Δ=2.2 mmu for formula $C_{20}H_{25}O_2N_6Br_2$ (M+H+); See Table 1 for $^1H$ and $^{13}C$ NMR data.

TABLE 1

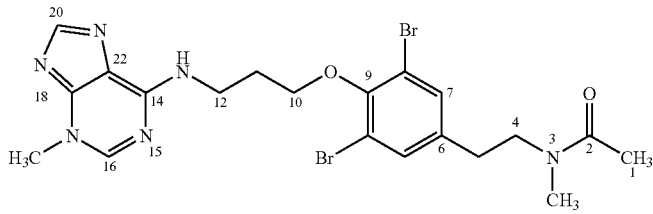

Aphrocallistin A
NMR data for Aphrocallistin A (d4-methanol, 600 MHz)

| Position | $^{13}C\ \delta$ | Aphrocallistin A multiplicity | $^{15}N\ \delta^1$ | $^1H\ \delta$ | multiplicity | COSY[2] | HMBC[3] |
|---|---|---|---|---|---|---|---|
| 1 | 20.0 | $CH_3$ | | 2.02 | s 3 H | | |
| 2 | 173.4 | C | | | | | H-1abc, N-3-$CH_3$, H-4ab |
| 3 | | | 111.5 | | | | H-1abc, H-5ab |
| 4 | 50.1 | $CH_2$ | | 3.50 | 2 H dd J = 7.6, 7.6 | H-5ab | N3-$CH_3$abc, H-5ab |
| 5 | 33.0 | $CH_2$ | | 2.74 | 2 H dd J = 7.6, 7.6 | H-4ab | H-4ab |
| 6 | 139.9 | C | | | | | H-4ab, H-5ab |
| 7 | 134.4 | CH, 2C | | 7.45 | 2 H, s | | H-5ab, H-7' |
| 8 | 118.9 | C, 2C | | | | | H-7 |
| 9 | 152.7 | C | | | | | H-7, H-10ab |
| 10 | 71.9 | $CH_2$ | | 4.11 | 2 H m | H-11ab | H-11ab, H-12ab |
| 11 | 30.5 | $CH_2$ | | 2.27 | 2 H m | H-10ab, H-12ab | H-10ab, H-12ab |
| 12 | 40.4 | $CH_2$ | | 4.04 | 2 H m | H-11ab | H-10ab, H-11ab |
| 13 | | | 106.0 | | | | H-11ab |
| 14 | 153.5 | C | | | | | H-12ab, H-16 |
| 15 | | | 226.9 | | | | H-16 |
| 16 | 149.7 | CH | | 8.6 | s | | N17-$CH_3$abc |
| 17 | | | 148.7 | | | | H-16, N-17$CH_3$ |
| 18 | 149.0 | C br | | | | | N-17$CH_3$, H-20 |
| 19 | | | not observed | | | | |
| 20 | 145.6 | CH br | | 8.4 | s | | |
| 21 | | | not observed | | | | |
| 22 | 112.6 | C br | | | | | H-20 |
| N3-$CH_3$ | 36.9 | $CH_3$ | | 2.98 | 3 H, s | | H-4ab |
| N-17 $CH_3$ | 36.8 | $CH_3$ | | 4.06 | 3 H, s | | H-18 |

[1]$^{15}N$ chemical shifts detected indirectly through $^{15}N$—$^1H$ HMBC

[2]From H # to

[3]From atom at this position to H atoms listed

TABLE 2

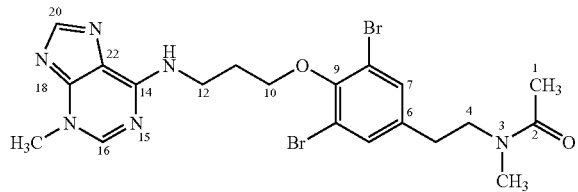

Aphrocallistin B
NMR data for Aphrocallistin B (d4-methanol, 600 MHz)

| position | $^{13}C$ | $^{15}N$ | $^{1}H$ | multiplicity |
|---|---|---|---|---|
| 1 | 20.89 | | 1.84 | 3 H s |
| 2 | 173.26 | | | |
| 3 | | 111.5 | | |
| 4 | 52.96 | | 3.55 | 2 H, dd J = 6.9, 6.9 |
| 5 | 33.92 | | 2.82 | 2 H, dd J = 6.9, 6.9 |
| 6 | 139.38 | | | |
| 7 | 134.61 | | 7.47 | 2 H, s |
| 8 | 119.14 | | | |
| 9 | 153.06 | | | |
| 10 | 71.9 | | 4.11 | 2 H m |
| 11 | 30.47 | | 2.27 | 2 H m |
| 12 | 40.35 | | 4.04 | 2 H m |
| 13 | | 106.0 | | |
| 14 | 153.5 | | | |
| 15 | | 226.9 | | |
| 16 | 149.7 | | 8.6 | s |
| 17 | | 148.7 | | |
| 18 | 149.0 | | | |
| 19 | | not observed | | |
| 20 | 145.6 | | 8.4 | s |
| 21 | | not observed | | |
| 22 | 112.6 | | | |
| N3-CH$_3$ | 33.76 | | 2.88 | 3 H s |
| N-17 CH$_3$ | 36.85 | | 4.06 | s 3 H |

Example 2

Antitumor Effects of the Mixture of Aphrocallistin A (I) and B(II)

A. Effects of Aphrocallistin A (I) and B(II) mixture on In Vitro Proliferation of Tumor Cell Lines.

Aphrocallistin A (I) and B(II) 3:2 mixture was analyzed as to its effects on the proliferation of a panel of tumor cell lines including both cell lines. The cell lines tested include: the NCI-ADR-RES (Formerly MCF-7/ADR) human ovarian carcinoma, DLD-1 human colorectal carcinoma, A549 human lung adenocarcinoma and PANC-1 human pancreatic carcinoma cell lines. A549, DLD-1, PANC-1, and NCI-ADR-RES cells were obtained from American Type Culture Collection, Rockville, Md. The A549, DLD-1, NCI-ADR-RES and PANC-1 cell lines are maintained in Roswell Park Memorial Institute (RPMI) medium 1640 supplemented with 100 U/mL penicillin 100 µg/ml streptomycin, 60 µg/ml L-glutamine, 18 mM HEPES, 0.05 mg/mL gentamycin and 10% fetal bovine serum (for the PANC-1 and DLD-1 cell lines, the media is also supplemented with 100 µg/ml sodium pyruvate and 2.5 mg/ml glucose). Cell lines are cultured in plastic tissue culture flasks and kept in an incubator at 37° C. in humidified air containing 5% $CO_2$. To assess the antiproliferative effects of agents against the various cell lines, 200 µl cultures (96-well tissue culture plates, Nunc, Denmark) are first established at $3 \times 10^4$ cells/ml for adherent lines (NCI ADR-RES, PANC-1) in tissue culture medium and incubated for 24 hr at 37° C. in 10% $CO_2$ in air in order to allow cells to attach. A volume of 100 µl of medium is removed from each test well and 100 µl of medium containing serial, two-fold dilutions of the test agent is added to each well containing tumor cells. Medium without drug is also added to wells containing tumor cells which serve as no drug controls. Positive drug controls are included to monitor drug sensitivity of each of the cell lines. These include varying dilutions of 5-fluorouracil and doxorubicin. After 72-h exposures tumor cells are enumerated using 3-[4,5-Dimethylthiazol-2-yl]-2,5-diphenyltetrazolium bromide (MTT) (M. C. Alley, et al., Cancer Res. 48:589, 1988) as follows:

A volume of 75 µl of warm growth media containing 5 mg/ml MTT is added to each well, cultures returned to the incubator, and left undisturbed for 3 hours. To spectrophotometrically quantitate formation of reduced formazan, plates are centrifuged (900×g, 5 minutes), culture fluids removed by aspiration, and 200 µl of acidified isopropanol (2 ml concentrated HCl/liter isopropanol) added per well. The absorbance of the resulting solutions is measured at 570 nm with a plate reader (BMG Labtech NOVOStar). The absorbance of tests wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, third ed., pp. 316-348, Charles Griffin Co., London, 1978). A linear relationship between tumor cell number and formazan production has been routinely observed over the range of cell densities observed in these experiments. The two standard drug controls (indicated above) are included in each assay to monitor the drug sensitivity of each of the cell lines and $IC_{50}$ values are determined for each drug-cell combination.

A summary of results in these assays for compound I can be found in Table 2.

TABLE 2

Cytotoxicity Results for Aphrocallistin A (I) and B(II) mixture

| | A549 $IC_{50}$ µg/mL | PANC-1 $IC_{50}$ µg/mL | NCI/ADR-RES $IC_{50}$ µg/mL | DLD-1 $IC_{50}$ µg/mL |
|---|---|---|---|---|
| Aphrocallistin A (I)/B(II) 3:2 mixture | 12.7 ± 3.7 | 13.1 ± 4.6 | 18.1 ± 0.7 | 3.7 ± 1.7 |

Example 3

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition comprising a first compound which is:

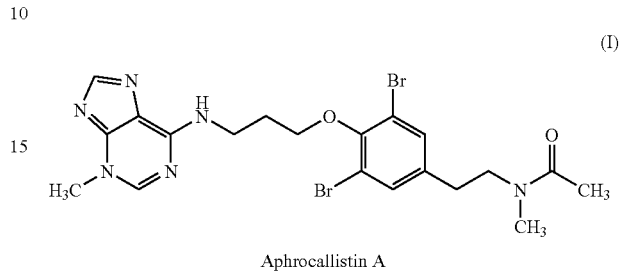

Aphrocallistin A and a second compound which is

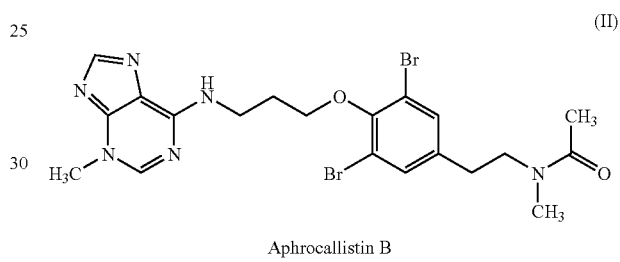

Aphrocallistin B wherein the ratio of the first compound to the second compound is 3:2.

* * * * *